United States Patent [19]

Chamberlin

[11] Patent Number: 5,025,107
[45] Date of Patent: Jun. 18, 1991

[54] PROCESS FOR COPRODUCTION OF ARYLENE DIAMINE DIHALIDES AND ALKYL HALIDES

[75] Inventor: Kim S. Chamberlin, Kingsport, Tenn.

[73] Assignee: Eastman Kodak Company, Rochester, N.Y.

[21] Appl. No.: 383,503

[22] Filed: Jul. 24, 1989

Related U.S. Application Data

[63] Continuation-in-part of Ser. No. 155,171, Feb. 9, 1988, abandoned.

[51] Int. Cl.$^5$ ............................................ C07C 209/62
[52] U.S. Cl. ................................. 564/414; 564/155; 570/261
[58] Field of Search ..................... 564/155, 207, 414; 570/261

[56] References Cited

U.S. PATENT DOCUMENTS

| | | | |
|---|---|---|---|
| 2,688,641 | 9/1954 | Girartis | 570/261 |
| 3,004,028 | 10/1961 | Dolliver et al. | 567/207 |
| 4,187,248 | 2/1980 | Merten et al. | 564/414 |
| 4,196,146 | 4/1980 | Merten et al. | 564/414 |
| 4,764,625 | 8/1988 | Turner et al. | 564/309 |
| 4,803,296 | 2/1989 | Steinmetz et al. | 570/261 |
| 4,815,564 | 7/1989 | Steinmetz et al. | 570/261 |

FOREIGN PATENT DOCUMENTS

| | | | |
|---|---|---|---|
| 0016831 | 1/1984 | Japan | 564/155 |
| 0611900 | 6/1978 | U.S.S.R. | 570/261 |
| 2087915 | 6/1982 | United Kingdom | 570/261 |

OTHER PUBLICATIONS

Surrey, "Ullman Reaction" and Ullman Condensation, *Name Reactions in Organic Chemistry*, 1954, pp. 162–164.

Merck, "Dimethyl Sulfate" and "Methyl Iodide", *The Merck Index, Tenth Edition*, 1983, pp. 474–475 & 872.

*Primary Examiner*—Richard L. Raymond
*Attorney, Agent, or Firm*—J. Frederick Thomsen; William P. Heath, Jr.

[57] ABSTRACT

Disclosed is a process for the preparation of bisacylamido aromatic compounds by reacting certain arylene dihalides with certain arylene dihalides in the presence of a copper catalyst. The process may be utilized in the synthesis of arylenediamines.

4 Claims, No Drawings

PROCESS FOR COPRODUCTION OF ARYLENE DIAMINE DIHALIDES AND ALKYL HALIDES

This application is a continuation-in-part of my copending application Ser. No. 155,171 filed Feb. 9, 1988, now abandoned.

This invention concerns a novel process for the preparation of aromatic diamines. More specifically, this invention concerns the reaction of certain arylenedihalides with certain amides or imides in the presence of a copper catalyst to obtain bis-acylamido aromatic compounds, contacting the reaction mixture with a dialkyl sulfate, recovering an alkyl halide and hydrolyzing the bis-acylamido compound to obtain an aromatic diamine.

The process of this invention provides a practical Procedure for the preparation of arylenediamines without the necessity of using high pressure equipment. For example, the bis-acylamido aromatic compounds may be hydrolyzed in the presence of hydrochloric acid to obtain arylenediamine hydrochlorides. Most known processes for manufacturing arylenediamines involve the catalytic hydrogenation of dinitro aromatic compounds under super atmospheric pressures.

The arylenedihalides which may be used in the process include the various isomeric arylenediiodides and arylenedibromides wherein the arylene residue can be unsubstituted or substituted phenylene of naphthylene radicals. Due to this reactivity and availability, the preferred arylenedihalides are 2,6- and 2,7-naphthylenediiodides and, especially, 1,4-phenylenediiodide. The amides useful in the process include primary carboxylic acid amides, particularly those having the formula

wherein R is an alkyl group of 1 to 4 carbon atoms or an aryl group such as phenyl. Acetamide is the most economical and thus is the preferred primary carboxylic acid amide. The useful amides also include lactams such as 2-pyrrolidinone (butyrolactam). The imides which may be used include imides of dicarboxylic acids such as phthalimide and succinimide.

The copper catalyst may be metallic copper, cuprous oxide or a wide variety of cuprous and cupric salts such as halides, nitrates, sulfates, and carboxylates. The copper catalyst preferably is a copper chloride, bromide, iodide, or acetate. The catalytically effective amount of copper catalyst generally is in the range of about 0.1 to 3.0 or higher mole percent based on the moles of arylene dihalide present. Normally, the amount of catalyst used is in the range of 0.5 to 1.0 mole percent based on the arylene dihalide reactant.

The reaction involved in the process of this invention requires the presence of a strong base such as an alkali metal, especially sodium or potassium, carbonate, hydroxide or carboxylate, e.g., acetate. The alkali metal base preferably is potassium or sodium carbonate since these bases, even when used in excess, do not interfere with the recovery of the halide ion of the arylene dihalide as an alkyl halide. The amount of strong base required normally should be at least two equivalents per mole of arylene dihalide. The use of a substantial excess of bases, although not detrimental to the process, offers no advantage and thus is not preferred. Typically the amount of base will be in the range of about 2.1 to 2.5 equivalents per mole of arylene dihalide.

The mole ratio of amide or imide to arylene dihalide is not important to the operability of the process. However, for satisfactory results the ratios normally should be at least 2 and, to ensure complete reaction of the arylene dihalide reactant, preferably is in the range of about 2.2 to 3 mole acylamide per mole of dihalide reactant.

The process provided by this invention is carried out at a temperature of at least 160° C., preferably at least 180° C. Although higher temperatures are permissible, the upper limit of the temperature is about 230° C., preferably 210° C. If desired, the process can be performed in the presence of an inert solvent such as a high boiling amide or lactam, e.g., N-methylpyrrolidinone. However, since the arylene dihalide functions as the solvent the use of an additional solvent is not necessary.

The process described hereinabove can be utilized advantageously as one step of a process for the preparation of arylenediamine hydrohalide while co-producing an alkyl halide. The process can be carried out in a single reactor and is especially useful in recovering iodide when the more reactive arylene diiodide is one of the starting materials. The process for preparing arylenediamine hydrohalides comprises the steps of:

(1) reacting an arylenedihalide with an amide or imide at a temperature of at least 160° C. in the presence of an alkali metal base and a copper catalyst to obtain an arylene bis-amide or arylene bis-imide;

(2) adding a dialkyl sulfate to the reaction mixture resulting from step (1);

(3) distilling an alkyl halide from the reaction mixture obtained from step (2); and (4) adding a hydrohalic acid to the remaining reaction mixture of step (3) and hydrolyzing the arylene bis-amide or arylene bis-imide to the corresponding arylenediamine hydrohalide.

sulfate added in step (2) preferably is dimethyl sulfate although any di-lower alkyl, e.g., alkyl of 1 to 4 carbon atoms, sulfate can be used. To maximize recovery of the alkyl iodide in step (3), the amount of dialkyl sulfate used should be at least 2 moles per mole of arylenedihalide starting material. Typically a slight to moderate excess of dialkylsulfate is used, e.g., from 2.05 to 2.3 moles per mole of arylenedihalide. The alkyl iodide then is distilled off at elevated pressure and/or reduced pressure.

Step (4) of the process is a conventional acid hydrolysis of an amide or imide using a hydrohalide acid, i.e., aqueous hydrogen halide, to obtain the corresponding arylenediamine hydrohalide which can be isolated by cooling the final solution mixture and filtering off the product. The hydrolysis can be completed by heating the reaction mixture and hydrohalide acid at temperatures in the range of 100° to 130° C. according to known amide hydrolysis procedure.

A particularly preferred embodiment of the four-step process comprises:

(1) reacting 1,4-phenylenediiodide with acetamide at a temperature of at least 180° C. in the presence of sodium or potassium carbonate and a catalytic amount of a copper catalyst to obtain 1,4-phenylene bis-acetamide;

(2) adding dimethyl sulfate to the reaction mixture resulting from step (1);

(3) distilling methyl iodide from the reaction mixture obtained from step (2); and (4) adding hydrochloric acid to the remaining reaction mixture of step (3) and hydrolyzing the phenylene bis-acetamide to 1,4-phenylenediamine dihydrochloride.

The process provided by my invention is further illustrated by the following example:

EXAMPLE 1,4-Diiodobenzene (0.1 mol), acetamide (1.0 mol), potassium carbonate (0.145 mol) and cuprous iodide (1.0 mol percent) are heated to 180° to 210° C. for two hours and cooled to 100° C. Water (100 mL) is added and the temperature is adjusted to 65° C. Dimethyl sulfate (20 mL, 0.2114 mol) is added over a 45 minute period while the methyl iodide formed is distilled off. The temperature then is raised to 120° C. and held at 120° C. for one-half hour to distill over 40 mL of volatiles. The mixture is cooled to 60° to 80° C., 37% hydrochloric acid (500 mL is added and the mixture is refluxed for two hours. The product is collected by cooling the mixture to 15° C., filtering, washing with concentrated hydrochloric acid (100 mL) and air drying. The amount of p-phenylenediamine dihydrochloride obtained is 80.9% by theory.

The invention has been described in detail with particular reference to preferred embodiments thereof, but it will be understood that variations and modifications can be effected within the spirit and scope of the invention.

I claim:

1. Process for the coproduction of an arylene diamine dihydrohalide and an alkyl halide which comprises the steps of:
   (1) reacting an arylene dihalide with an amide or imide at a temperature of at least 160° C. in the presence of an alkali metal base and a copper catalyst to form an arylene bis-amide or arylene bis-imide;
   (2) adding dialkyl sulfate to the reaction mixture resulting from step (1);
   (3) distilling an alkyl halide from the reaction mixture obtained from step (2); and
   (4) adding a hydrohalic acid to the remaining reaction mixture of step (3) and hydrolyzing the arylene bis-amide or arylene bis-imide to the corresponding arylene diamine hydrohalide, wherein the arylenedihalide is a dibromide or diiodide and the alkyl halide is a bromide or iodide.

2. Process according to claim 1 wherein step (1) comprises reacting 1,2- or 1,4-phenylenediiodide or 2,6- or 2,7-naphthylenediiodide with (i) an amide having the formula

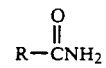

wherein R is an alkyl group of 1 to 4 carbon atoms or an aryl group, (ii) 2-pyrrolidinone, (iii) phthalimide or (iv) succinimide in the presence of sodium or potassium hydroxide, carbonate or acetate at a temperature of at least 180° C.

3. Process for the coproduction of an arylenediamine dihydrohalide and an alkyl halide which comprises:
   (1) reacting an arylenedihalide with a primary acylamide at a temperature of at least 180° C. in the presence of potassium or sodium carbonate and a catalytic amount of a copper catalyst to form an arylene bis-acylamide;
   (2) adding dialkyl sulfate to the reaction mixture resulting from step (1);
   (3) distilling an alkyl halide from the reaction mixture obtained from step (2); and
   (4) adding a hydrohalic acid to the remaining reaction mixture of step (3) and hydrolyzing the arylene bis-acylamide to the corresponding arylenediamine hydrohalide;

wherein the arylenedihalide is a dibromide or diiodide and the alkyl halide is a bromide or iodide.

4. Process according to claim 3 for the coproduction of 1,4-phenylenediamine hydrochloride and methyl iodide which comprises:
   (1) reacting 1,4-phenylenediiodide with acetamide at a temperature of at least 180° C. in the presence of sodium or potassium carbonate and a catalytic amount of a copper catalyst to form 1,4-phenylene bis-acetamine;
   (2) adding dimethyl sulfate to the reaction mixture resulting from step (1);
   (3) distilling methyl iodide from the reaction resulting from step (2); and
   (4) adding hydrochloric acid to the remaining reaction mixture of step (3) and hydrolyzing the phenylene bis-acetamide to phenylenediamine dihydrochloride.

* * * * *